United States Patent [19]

Yoon

[11] Patent Number: 5,330,432
[45] Date of Patent: Jul. 19, 1994

[54] RETRACTABLE SAFETY PENETRATING INSTRUMENT

[76] Inventor: InBae Yoon, 2101 Highland Ridge Dr., Phoenix, Md. 21131

[21] Appl. No.: 805,506

[22] Filed: Dec. 6, 1991

[51] Int. Cl.$^5$ .................................. A61M 5/00
[52] U.S. Cl. .............................. 604/164; 604/169; 604/272
[58] Field of Search ................ 604/117, 164–169, 604/264, 272–274; 606/184, 185, 191

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |
| 5,152,754 | 10/1992 | Plyley et al. . |
| 5,158,552 | 10/1992 | Borgia et al. . |

FOREIGN PATENT DOCUMENTS 2544262 4/1977 Fed. Rep. of Germany .
1435246 11/1988 U.S.S.R. .

Primary Examiner—Randall L. Green
Assistant Examiner—Mary Beth Jones

[57] ABSTRACT

A retractable safety penetrating instrument includes a cannula and a needle disposed within the cannula and supported in a manner to automatically move proximally from an extended position wherein a sharp distal end of the needle protrudes from the cannula to a retracted position wherein the sharp distal end of the needle is protected in response to distal movement of the retractable safety penetrating instrument upon penetration into a cavity in the body. A retracting mechanism moves the needle proximally, is normally locked in a position preventing proximal movement of the needle and is released by distal movement of an operating member to trigger retraction of the needle.

42 Claims, 3 Drawing Sheets

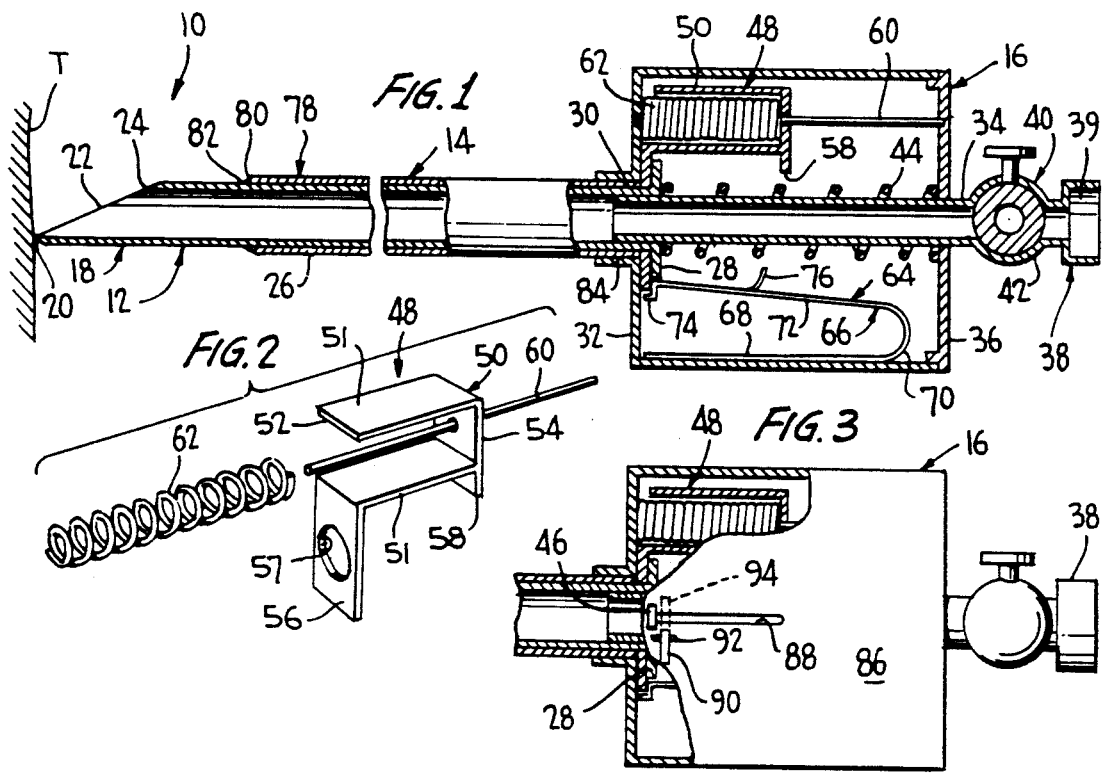
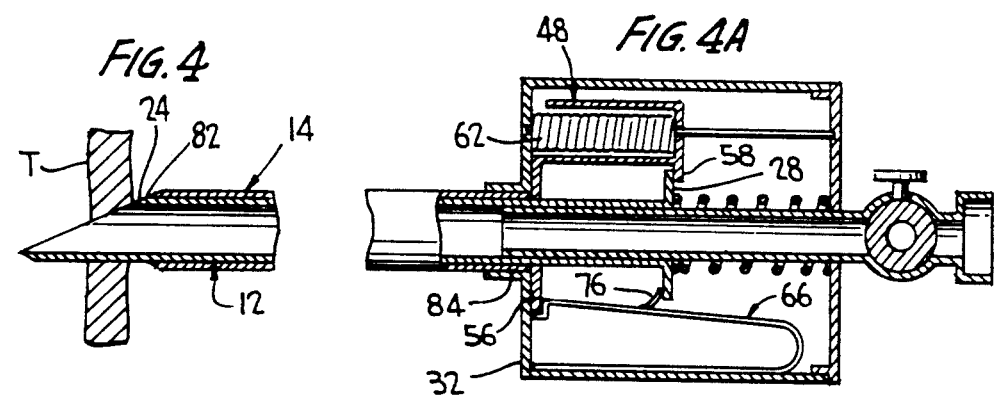
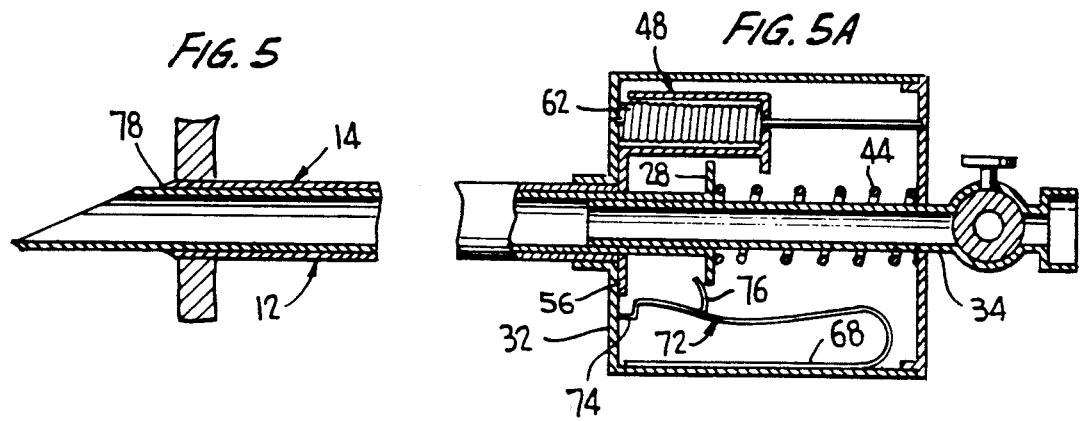

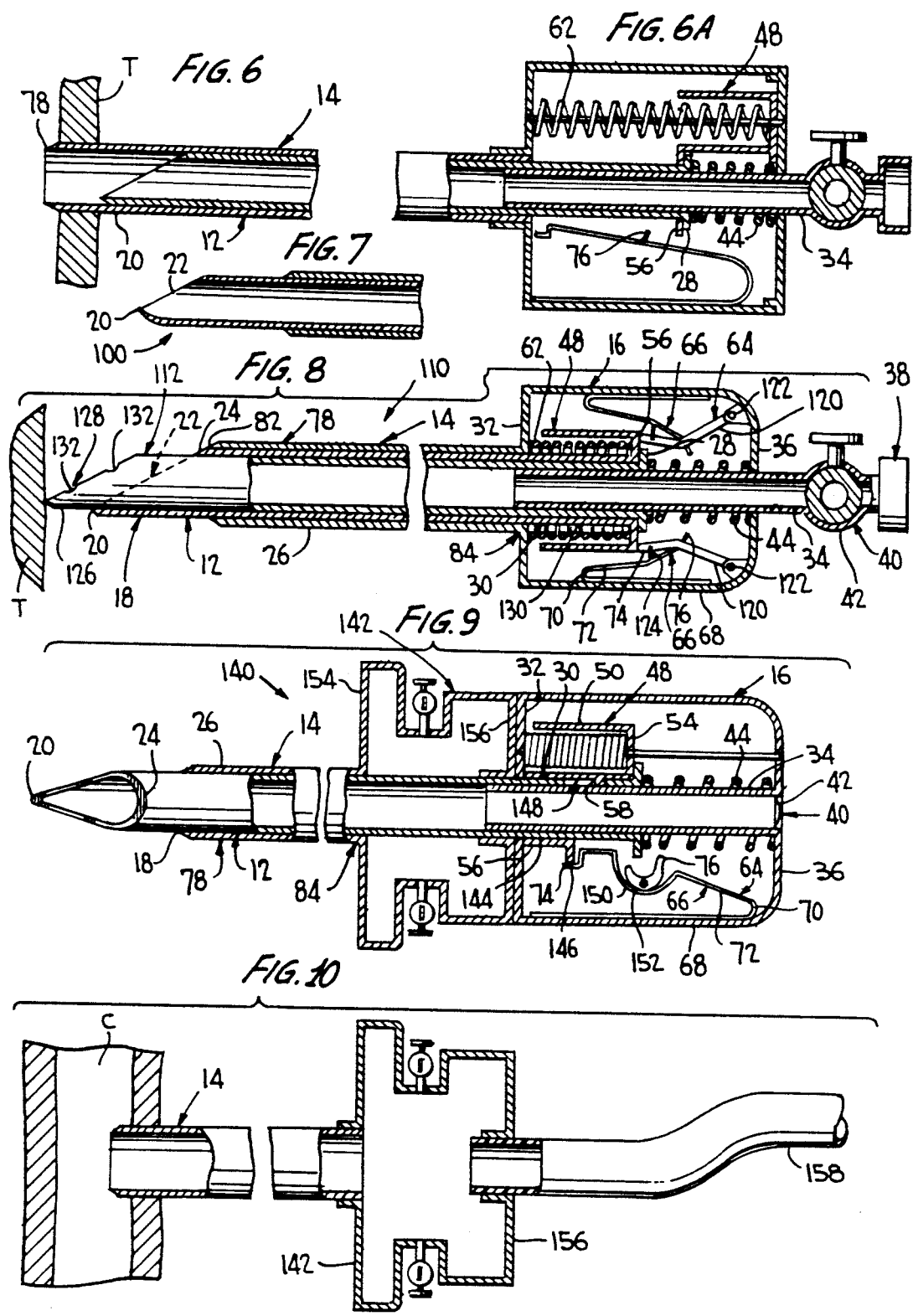

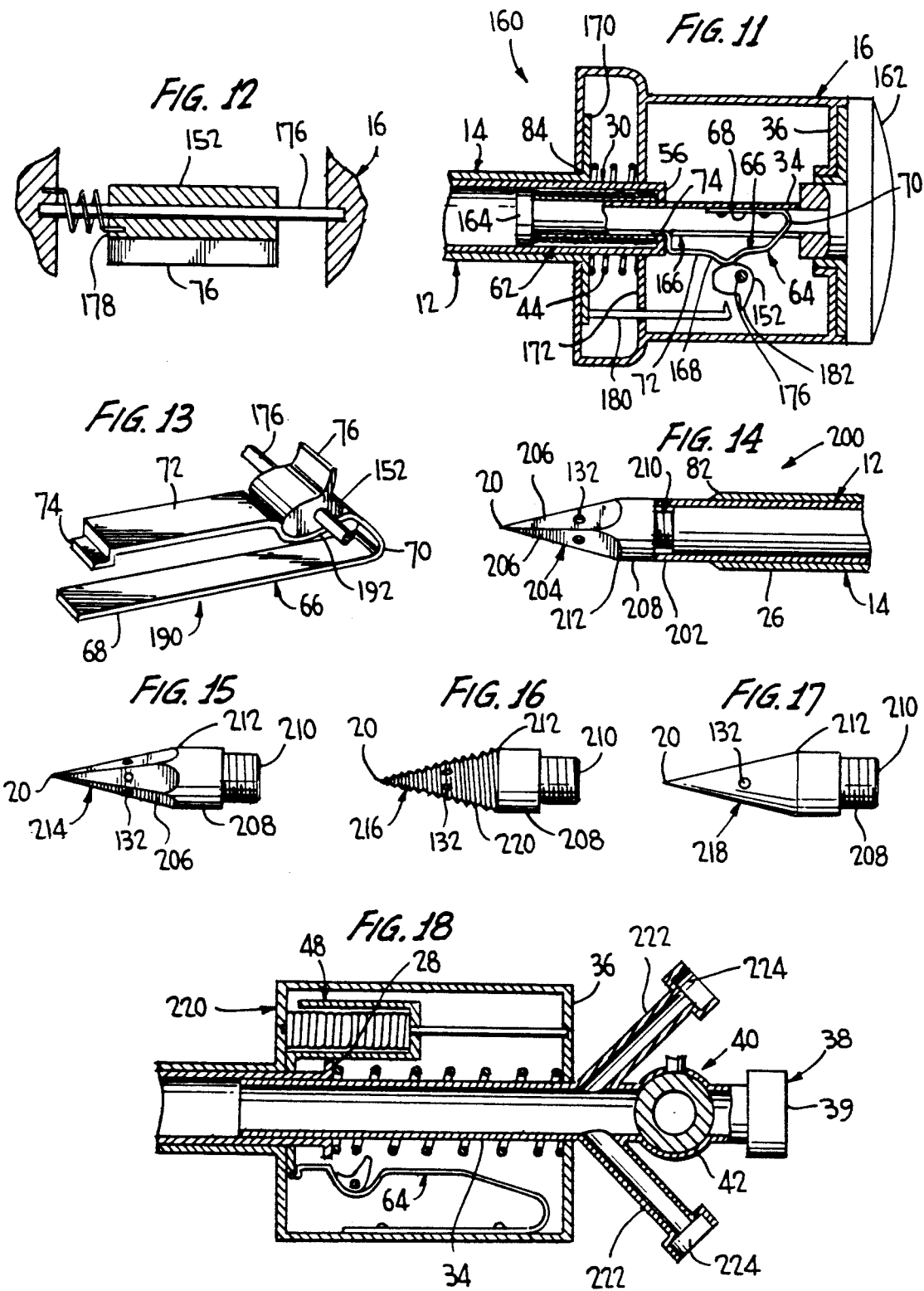

RETRACTABLE SAFETY PENETRATING INSTRUMENT

BACKGROUND OF THE INVENTION

1. Field of the Invention

The present invention pertains to safety penetrating instruments and, more particularly, to safety penetrating instruments having cannulas or sleeves for introduction into anatomical cavities and needles disposed within the cannulas with sharp tips for penetrating cavity walls.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricle and spinal and synovial cavities, with access being established via a sleeve or cannula positioned during penetration into the cavity with the penetrating instrument. Such penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to prevent the sharp tip of the penetrating member from inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety penetrating instruments including a safety probe biased to extend beyond the sharp tip of a penetrating member have become widely accepted for use in penetrating anatomical cavities. For example, the Verres needle, commonly used to create a pneumoperitoneum, has a spring-loaded inner member disposed within a tubular needle. U.S. Pat. No. 1,527,291 to Zoraquin, U.S. Pat. No. 2,623,521 to Shaw and U.S. Pat. No. 2,630,803 to Baran are exemplary of safety penetrating instruments with a spring-loaded inner member disposed in a needle, while U.S. Pat. No. 4,254,762 to Yoon shows an endoscope spring-biased in a hollow needle. German Offenlegungsschrift 2,544,262 discloses an intrauterine catheter including a tube having a distal sharp point, a spring-biased blunt member in the tube distal end and a hose or catheter slidable over the tube.

Safety trocars having a spring-biased protective shield disposed between an outer sleeve and an inner trocar are marketed by Ethicon, Inc. as the Endopath and by United States Surgical Corp. as the Surgiport. U.S. Pat. No. 4,535,773 to Yoon, U.S. Pat. No. 4,601,710 to Moll and U.S. Pat. No. 4,654,030 to Moll et al are illustrative of such safety trocars. A trocar disposed within a portal sleeve and retractable within the sleeve in response to an electrical signal generated when force from tissue contact is removed from the sharp tip of the trocar is set forth in U.S. Pat. No. 4,535,773 to Yoon.

While prior art safety penetrating instruments are widely used, they suffer from many disadvantages when used in the procedures for which they are presently recommended; and, additionally, prior art safety penetrating instruments cannot be used in many procedures for which safety of penetration is highly desirable along with introduction of an outer sleeve or cannula. One of the disadvantages of prior art safety penetrating instruments is that the safety probes protrude from the sharp tips of the penetrating members to protect the sharp tips upon penetration through tissue of the cavity wall such that tissue and organ structures can be damaged by the safety probe. Accordingly, safe penetration into small or narrow anatomical cavities can not be accomplished for many various procedures. Another disadvantage of prior art safety penetrating instruments is that the safety probes can produce an irregular surface or profile with the sharp tips of the penetrating members during penetration of tissue resulting in increased resistance during penetration of a cavity wall, trauma and damage to tissue and possible jamming and trapping of tissue.

There is a great need for a safety penetrating instrument than can be used to penetrate small cavities, such as veins, while reducing the opportunity for injury to tissue in or forming the cavity and, in particular, for an instrument where the needle or penetrating member is positioned in an enclosed position even when left in place in the cannula introduced with the needle.

SUMMARY OF THE INVENTION

Accordingly, it is a primary object of the present invention to overcome the above mentioned disadvantages of prior art safety penetrating instruments.

Another object of the present invention is to automatically retract a needle of a safety penetrating instrument to a protected position in response to distal movement of the safety penetrating instrument after a distal end of a cannula enters a body cavity.

A further object of the present invention is to arrange an operating member in a safety penetrating instrument such that movement of the operating member distally causes the needle to retract to a protected, safe position within the instrument.

It is also an object of the present invention to automatically retract a needle of a retractable safety penetrating instrument to a protected position in response to distal movement of a safety probe prior to the safety probe protruding beyond the sharp tip of the needle.

The present invention has an additional object of allowing safe introduction of cannulas into body cavities of very small size, such as veins, arteries, spinal, synovial, pleural or pericardial cavities, for example, and for intricate use, such as suprapubic procedures, by automatically retracting a sharp tip of a needle after the cavity is penetrated thereby minimizing the extension of the safety penetrating instrument into the cavity.

Yet another object of the present invention is to provide a method of safely penetrating various anatomical cavities by automatically retracting a needle upon entry into a cavity in response to a mechanical distal movement of a component of a safety penetrating instrument.

A further object of the present invention is to provide a retractable safety penetrating instrument including a cannula and a distally biased needle disposed within the cannula and having a sharp tip retractable to a protected position in response to movement of the needle due to the distal bias upon penetration through tissue of a cavity wall.

A still further object of the present invention is to provide a retractable safety penetrating instrument including a distally biased cannula and a needle disposed within the cannula and having a sharp tip retractable to a protected position in response to movement of the cannula due to the distal bias upon penetration through tissue of a cavity wall.

An additional object of the present invention is to provide a retractable safety penetrating instrument having a cannula, a needle disposed within the cannula and a distally biased safety probe disposed within the needle with a sharp tip of the needle being retractable to a protected position in response to movement of the safety probe due to the distal bias upon penetration through tissue of a cavity wall.

Another object of the present invention is to protect the sharp tip of a tubular or hollow needle in a safety penetrating instrument without requiring a safety probe within the needle by automatically retracting the needle into a cannula to shield the sharp tip from contact with tissue upon cavity penetration.

Some of the advantages of the present invention over the prior art are that small or narrow anatomical cavities can be safely penetrated, an outer sleeve or cannula, such as a catheter, can safely be introduced into anatomical cavities of very small size for many various procedures in many areas including, for example, cardiac, brain, vascular, chest, genitourinary, suprapubic, and spinal fields, safe penetration of cavities can be accomplished without parts of the safety penetrating instrument protruding beyond the sharp tip of the penetrating member upon penetration into the cavities as is particularly desirable where organ structures adhere to cavity walls or the cavities are very small or narrow, the risk of developing a hematoma when penetrating veins and arteries is reduced, the retractable safety penetrating instrument encourages the use of a smooth, continuous penetrating motion by the surgeon thereby reducing trauma, tears and irregular surfaces in the tissue of the cavity wall, the retractable safety penetrating instrument can be used to penetrate anatomical cavities of the type containing organ structures that could be injured by contact with even a blunt instrument part such as a safety probe, with use of a safety probe, the sharp tip of the needle can be protected prior to penetration of tissue ensuring safety of medical personnel during use, with the use of a threaded tip on the needle, penetration of the narrowest of anatomical cavities can be achieved in a safe manner in view of the gradual advancement of the needle coupled with immediate, automatic retraction of the needle upon entry of the distal end of the instrument into the cavity, with the use of a curved needle, penetration can be achieved with a spoon-like scooping or curving motion, safe penetration is achieved while permitting injection or evacuation of fluids, trauma and damage to tissue is minimized, tissue jamming and trapping is avoided and safety penetrating instruments according to the present invention can be inexpensively manufactured to be reusable or disposable for universal use.

The present invention is generally characterized in a retractable safety penetrating instrument including a cannula and a needle disposed within the cannula and supported in a manner to automatically move proximally from an extended position protruding from the cannula to a safe retracted position in response to distal movement of the retractable safety penetrating instrument. Retraction of the needle is caused by a strong bias spring that is normally locked in a compressed state by a latch and is released by the distal movement of an operating member to trigger the retraction of the needle. The latch and trigger are spring loaded to normally lock the penetrating member against retraction and to be moved out of locking engagement by flexing of the spring via movement of a cam, an off-center pivot or a leaf of a spring in response to the distal movement. The retraction of the needle can be responsive to distal movement of the needle, the cannula or any other operating member, such as a probe mounted in the needle.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 1 is a broken view, partly in section, of a retractable safety penetrating instrument according to the present invention.

FIG. 2 is a perspective view of the retracting mechanism of the retractable safety penetrating instrument of FIG. 1.

FIG. 3 is a broken view, partly in section, of the housing of the retractable safety penetrating instrument of FIG. 1.

FIGS. 4, 5 and 6 illustrate the relative position of the cannula and the needle of the retractable safety penetrating instrument of FIG. 1 during sequential stages of penetration of tissue of an anatomical cavity wall.

FIGS. 4A, 5A and 6A illustrate the relative positions of the operating member, the locking and releasing mechanism and the retracting mechanism of the retractable safety penetrating instrument of FIG. 1 during the corresponding stages of penetration of FIGS. 4, 5 and 6.

FIG. 7 is a broken sectional view of a modification of the distal end of the needle of the retractable safety penetrating instrument according to the present invention.

FIG. 8 is a broken view, partly in section, of a modification of the retractable safety penetrating instrument according to the present invention.

FIG. 9 is a broken view, partly in section, of a further modification of the retractable safety penetrating instrument according to the present invention.

FIG. 10 is a broken view, partly in section, showing the cannula of the retractable safety penetrating instrument of FIG. 9 introduced into a tubular vessel with the coupling coupled with an intravenous tube.

FIG. 11 is a broken sectional view of the housing of a further modification of the retractable safety penetrating instrument according to the present invention.

FIG. 12 is a cross-sectional view taken through line 12—12 of FIG. 11.

FIG. 13 is a perspective view of a modification of the locking and releasing mechanism of the retractable safety penetrating instrument according to the present invention.

FIG. 14 is a broken view, partly in section, of a modification of the distal end of the retractable safety penetrating instrument according to the present invention.

FIGS. 15, 16 and 17 are side views of modifications of the distal tips for use on the needle of the retractable safety penetrating instrument according to the present invention.

FIG. 18 is a broken sectional view of the housing of a further modification of the retractable safety penetrating instrument according to the present invention.

DESCRIPTION OF THE PREFERRED EMBODIMENTS

A retractable safety penetrating instrument 10 according to the present invention is illustrated in FIG. 1 and includes an elongate penetrating member or needle 12, an outer sleeve or cannula 14 concentrically disposed around needle 12 and a housing 16 mounting needle 12 and cannula 14. Needle 12 is preferably made of stainless steel with a cylindrical body having an outer diameter and wall thickness dependent upon the medical procedure to be performed and the anatomical cavity to be penetrated. The outer diameter of the needle will typically range in size from 16 gauge to 25 gauge with 18 gauge being desirable for use as an intravenous needle, although larger and smaller diameter needles can be utilized. The needle 12 has a distal end 18 terminating at a sharp tip or point 20 for penetrating anatomical tissue. The needle 12 can be solid or cannulated, and the distal end 18 can have various hollow or solid geometrical configurations. As shown in FIG. 1, the needle 12 is hollow or cannulated and has a distal end surface 22 disposed at an acute angle with a longitudinal axis of the needle, the end surface 22 having a trailing edge or junction 24 proximally joining the end surface to an elongated, cylindrical body 26. Cylindrical body 26 extends proximally from trailing edge 24 to an operating member or flange 28 at a proximal end 30 of the needle, the proximal end 30 being disposed in housing 16 with cylindrical body 26 passing through an opening in a front wall 32 of the housing. The proximal end 30 of the needle 12 is mounted on a cylindrical member or tube 34 extending through an opening in an end wall 36 of housing 16 and into the proximal end 30 of the needle. Tube 34 terminates externally of housing 16 at a hub 38 having an opening 39 therein communicating with the lumen of tube 34. A valve assembly 40, such as stop cock 42, is mounted on tube 34 externally of housing 16 to control flow through the tube and, therefore, the needle 12, and for additional confirmation of cavity penetration via leakage detection. A helical coil spring 44 is disposed around tube 34 and mounted in compression between flange 28 and end wall 36 of housing 16 to bias the needle 12 in a distal direction. A knob 46 is threadedly secured along the periphery of flange 28 as shown in FIG. 3; and, to simplify assembly of the retractable safety penetrating instrument, flange 28 can be removably secured to cylindrical body 26 such as by threads and the like. Cylindrical body 26 can be hollow or tubular along the length of the needle 12 as shown or the cylindrical body can be solid or partly hollow or tubular depending upon manufacturing techniques utilized and the construction of the distal end 18 of the needle. The cylindrical body 26 can be splined to tube 34 or cannula 14 to prevent rotation of the needle 12 relative to the cannula and assure angular alignment at the distal end of the retractable safety penetrating instrument. While the distal end of the needle 12 is shown as being angled with a cannulated configuration, the distal end can have other solid or hollow geometric configurations, and other types of penetrating members can be used with the retractable safety penetrating instrument.

A retracting mechanism 48 as shown in FIGS. 1 and 2 is mounted on the proximal end 30 of the needle 12 to be disposed in housing 16 and includes a rail 50 formed of flat, parallel, opposing sides 51 defining an open distal end 52 and a proximal end closed by an abutment wall 54 and a plate 56 extending perpendicularly from one of the sides 51 at distal end 52. An abutment member, such as a pin or protrusion 58, extends from a side 51 of the rail 50 in the same direction as plate 56. Cylindrical body 26 of the needle 12 extends through an opening 57 in plate 56 such that flange 28 is mounted between plate 56 and pin 58, with flange 28 being biased against plate 56 by spring 44. A connecting rod 60 has ends secured to the front and end walls 32 and 36, respectively, of housing 16, the rod 60 passing longitudinally through the rail 50 via an opening in abutment wall 54. A helical retracting spring 62, stronger than spring 44, is disposed around connecting rod 60 within the rail 50 and is mounted in compression between front wall 32 of housing 16 and abutment wall 54 of rail 50 to bias the retracting mechanism 48 and, via abutment with flange 28, the needle 12, in a proximal direction.

A locking and releasing mechanism 64 for the retracting mechanism 48 is mounted in housing 16 and includes a latch or locking spring 66 having a substantially flat base 68 secured to a side wall of housing 16 and terminating proximally at a bend 70 and an arm 72 joined to bend 70 and extending angularly, distally therefrom in the direction of a longitudinal axis of the retractable safety penetrating instrument. A bent locking finger 74 on a distal end of the arm 72 engages plate 56 and holds the plate against front wall 32 of the housing 16 to prevent movement of the retracting mechanism 48 in a proximal direction, the finger 74 being spring-biased into engagement with plate 56. Arm 72 is bifurcated to form a releasing or trigger member including a trigger or leaf 76 extending from arm 72 angularly, proximally in the direction of the longitudinal axis and spring-biased to a rest position shown in FIG. 1 wherein the trigger 76 is disposed proximally of flange 28 in the path of movement of the flange along tube 34 with plate 58 held against front wall 32. The latch can be mounted at any suitable location on the housing and provided with a configuration to act as a stop or abutment to prevent proximal movement of the retracting mechanism and to be actuated or released by a trigger. The latch and trigger can be made as one piece or multiple pieces dependent upon the housing construction and the operating member for engaging the trigger, flange 28 in retractable safety penetrating instrument 10.

Outer sleeve 14 can be a cannula, such as a catheter or the like, and is preferably made of a cylindrical length of medically acceptable, plastic material that can be rigid or flexible and transparent or opaque. The cannula 14 has a distal end 78, that can be acutely angled or beveled at the same angle as trailing edge 24 as shown at 80, terminating at a peripheral edge 82 and a proximal end 84 secured to front wall 32 of housing 16. The cannula has a wall thickness and outer diameter dependent upon the anatomical cavity to be penetrated and the medical procedure to be performed and an inner diameter sized to closely receive the outer diameter of the needle such that there is minimal gap or space between the cannula and the needle.

Housing 16 is preferably made of plastic to reduce cost and has a configuration in cross-section producing an external profile facilitating grasping during use. Housing 16 can be rectangular in cross-section including four side walls extending from front wall 32 to end wall 36 with one side wall, indicated at 86 in FIG. 3, having a slot 88 therein disposed parallel with the longitudinal axis of the retractable safety penetrating instrument and receiving knob 46. A lock 90 is mounted externally along wall 86 on a hinge 92 such that the lock 90 can be pivoted between an unlocked position wherein the lock does not block movement of knob 46 along slot 88 and a locked position shown in broken lines at 94 in FIG. 3 wherein the lock is disposed transverse to slot 88 abutting knob 46 to block proximal movement of the knob and, therefore, the needle.

In order to assemble the retractable safety penetrating instrument 10, the proximal end 30 of the needle 12 is assembled in housing 16 as shown in FIG. 1 with plate 56 of retracting mechanism 48 held against front wall 32 of the housing by latch 66 against the proximal bias of retracting spring 62. Needle 12 is biased distally by spring 44 such that operating flange 28 is biased against plate 56 and is disposed distally of trigger 76. With needle 12 biased distally by spring 44, trailing edge 24 is disposed distally of peripheral edge 82.

In a method of operation for the retractable safety penetrating instrument 10, the latch 66 is normally in the position shown in FIG. 1 with trigger 76 in the rest position and finger 74 engaging a proximal face of plate 56 such that the retracting mechanism 48 cannot move proximally and is, therefore, locked with the plate held against front wall 32 of housing 16. Spring 44 is normally in the position shown in FIG. 1 such that the needle 12 is biased distally with peripheral edge 82 of the cannula 14 disposed proximally of trailing edge 24 as shown in FIG. 1 just prior to penetration of tissue T of an anatomical cavity wall. When tissue T is to be penetrated, the housing 16 is gripped in one hand and the retractable safety penetrating instrument is forced into the tissue T as shown in FIG. 4. The needle 12 will move proximally against the distal bias of spring 44 due to the proximal force from tissue contact at the distal end 18 of the needle such that trailing edge 24 will be aligned with peripheral edge 82 to present a substantially smooth profile facilitating penetration of tissue and avoiding jamming and trapping of tissue. Accordingly, the needle 12 and the cannula 14 will be stable during penetration of the tissue T and will move together through the tissue. Operating flange 28 will abut the pin 58 serving as a positive stop limiting proximal movement of the needle 12 as shown in FIG. 4A. The operating flange 28 will have moved proximally past the trigger 76; however, this movement does not disengage the latch 66 from the plate 56 and the trigger returns to the rest position as soon as the operating flange has moved proximally therepast. Once the distal end 78 of the cannula 14 has entered the anatomical cavity, as shown in FIG. 5, such that the force from tissue contact is removed from the distal end of the retractable safety penetrating instrument, the needle 12 will be moved distally due to the distal bias of spring 44. As the needle 12 moves distally, operating flange 28 moves distally to engage the trigger 76 and pull the trigger distally forcing the arm 72 in a direction outwardly from the longitudinal axis and toward base 68 such that finger 74 is released from plate 56 of the retracting mechanism 48 as shown in FIG. 5A. Once released, the retracting mechanism 48 will move proximally due to the strong retracting spring 62 overriding the distal bias of spring 44, and the retracting mechanism 48 will carry the needle 12 proximally along the tube 34 due to abutment of plate 56 with operating flange 28, the tube 34 guiding proximal movement of the needle. With the needle 12 moved proximally by the retracting mechanism 48, the sharp tip 20 of the needle is retracted within the distal end 78 of the cannula 14, as shown in FIG. 6, and the operating flange 28 is positioned proximally of trigger 76 as shown in FIG. 6A, the trigger having returned to the rest position. When it is desired to reset the retractable safety penetrating instrument 10 for further use, the knob 46 is grasped and manually moved distally along the slot 88 in housing 16 moving the needle 12 and the retracting mechanism 48 distally past the trigger 76 until plate 56 abuts the front wall 32 of the housing and is held thereagainst by finger 74 of the latch 66. Cannula 14 can remain in place in the cavity and various other devices, such as tubes, syringes or catheters, can be secured to hub 38 for introducing or withdrawing fluid from the cavity via the needle 12.

By varying the axial position of trigger 76 in the path of movement of the operating flange 28, the distance that the needle can move distally before the operating flange releases the retracting mechanism 48 upon penetration into an anatomical cavity can be controlled. In other words, the distance that the sharp tip 20 of the needle 12 is allowed to protrude beyond the peripheral edge 82 of the cannula 14 upon penetration into an anatomical cavity can be varied or adjusted by positioning the trigger to be disposed distally a greater or lesser distance from the operating flange after the flange has moved proximally during penetration. With the trigger 76 positioned distally of operating flange 28 a lesser distance, the needle 12 will move distally a relatively shorter distance before retracting mechanism 48 is released and, with the trigger positioned distally of the operating flange a greater distance, the needle will move distally a relatively greater distance before the operating flange triggers the retracting mechanism. Accordingly, the needle need protrude only a minimal distance from the cannula before the retracting mechanism is released upon penetration into an anatomical cavity such that safe penetration of small or narrow anatomical cavities is assured and injury to tissue and organ structure is prevented.

Although springs 44 and 62 are shown as coil springs, other types and configurations of springs as well as various other devices can be utilized to bias the needle and the retracting mechanism. It will be appreciated that the needle and the retracting mechanism can be biased in many ways and that springs 44 and 62 can be replaced with various devices, including flexible, compressible and resilient devices, capable of applying a directional biasing force.

The positive stop can include the pin and rail arrangement shown as well as other positive stop construction, and the positive stop can be provided at the distal or proximal end of the retractable safety penetrating instrument.

Rail 50 can have various non-cylindrical and cylindrical configurations; and, in modified form, the rail can be formed as a cylinder with abutment wall 54 at a proximal end and plate 56 extending perpendicularly from the cylinder at a distal end thereof. Additionally, plate 56 can have various surface configurations, such as circular, rectangular and square, and can be provided with an extension or ledge extending perpendicularly therefrom in a proximal direction with the finger 74 engaging the ledge to prevent proximal movement of the retracting mechanism 48. The distance that the ledge extends proximally from the plate 56 can be varied to accommodate locking springs of various lengths and configurations and to control the distance that knob 46 must be moved along slot 88 before the finger 74 will engage the retracting mechanism 48 when resetting the retractable safety penetrating instrument.

It will be appreciated that knob 46 is shown by way of example and that many other types of knobs or handles can be employed for resetting the retractable safety penetrating instrument. As a further example, an L-shaped handle can be attached to operating flange 28 allowing the slot 88 to be located at various other positions along the side walls of the housing 16 and not only the central position shown in FIG. 3.

Numerous other types of releasing or trigger members can be utilized in addition to leaf 76 for releasing or disengaging the latch 66 from the retracting mechanism 48. The locking and releasing mechanism 64 can be of multi-part construction or of integral, unitary construction, and various types of actions including camming, bending, buckling and spring actions and related components can be employed for releasing the latch 66 from the retracting mechanism 48.

It will be appreciated that the retracting mechanism, the locking and releasing mechanism, the operating member, the bias springs and the positive stop are illustrative only and that the retracting mechanism, the locking and releasing mechanism, the operating member, the bias springs, and the positive stop can have the various configurations and arrangements shown in applicant's co-pending patent application entitled "Retractable Safety Penetrating Instrument for Portal Sleeve Introduction" and filed on Nov. 27, 1991, which is incorporated herein by reference.

A modification of the distal end of the needle 12 for the retractable safety penetrating instrument according to the present invention is shown in FIG. 7 at 100. The distal end 100 is open and includes an acutely angled distal end surface 22, with a portion of the distal end 100 curving toward the longitudinal axis of the needle 12 to terminate at a sharp tip 20 laterally or radially disposed from the wall of the needle. The distal end configuration 100 is particularly advantageous for insertion into a wall of an anatomical cavity with a spoon-like, scooping or curving motion.

. A modification of a retractable safety penetrating instrument according to the present invention is shown in FIG. 8 at 110. The retractable safety penetrating instrument 110 includes needle 12, cannula 14 concentrically disposed around needle 12, a safety probe 112 disposed within needle 12 and housing 16 mounting needle 12, cannula 14 and safety probe 112. The needle 12 is cannulated and has an open distal end 18 with an end surface 22 disposed at an acute angle with a longitudinal axis of the needle and a proximal end 30 disposed in housing 16. End surface 22 terminates distally at sharp tip 20 and is joined proximally to cylindrical body 26 at trailing edge 24, the cylindrical body 26 extending proximally from trailing edge 24 to a proximal end 30 disposed in housing 16. A retracting mechanism 48 is mounted on proximal end 30 of the needle 12 and includes a plate 56 extending radially from the periphery of cylindrical body 26, an annular skirt 118 extending distally from plate 56 toward a front wall 32 of housing 16 and strong retracting spring 62 disposed concentrically around the cylindrical body 26 of the needle within skirt 118. The retracting spring 62 is mounted in compression between the front wall 32 of the housing 16 and the plate 56 such that the needle 12 is biased in a proximal direction. Locking and releasing mechanism 64 is disposed in housing 16 and prevents proximal movement of the retracting mechanism 48 and, therefore, the needle 12. The locking and releasing mechanism 64 includes a latch having locking bars 120 biased by locking springs 66 into engagement with plate 56. Locking bars 120 are pivotably secured at 122 to end wall 36 of housing 16 on diametrically opposite sides of tube 34 and extend angularly, distally toward a longitudinal axis of the retractable safety penetrating instrument, the locking bars 120 terminating distally at fingers 74 angled from the locking bars in a direction outwardly from the longitudinal axis. Locking springs 66 bias the locking bars 120 in a direction inwardly toward the longitudinal axis such that the fingers 74 engage plate 56 and prevent proximal movement of the needle 12. Each locking spring 66 includes a substantially flat base 68 secured to a side wall of the housing 16 and extending distally to a bend 70 and an arm 72 extending angularly, proximally from bend 70 in the direction of the longitudinal axis. Arms 72 are bifurcated to define connecting webs 124 connecting springs 66 with fingers 74 to position the fingers in engagement with plate 56 and releasing or trigger members including triggers or leaves 76 spring biased to a rest position shown in FIG. 8. The safety probe 112 includes a blunt distal end 126 with an angled end surface 128 disposed at an acute angle with a longitudinal axis of the retractable safety penetrating instrument that is the same as the acute angle of distal end surface 22 of needle 12 and a hollow proximal end 130 terminating at operating flange 28 disposed within housing 16 proximally of plate 56, the safety probe passing through an opening in plate 56. Apertures 132 are provided in end surface 128. Tube 34 extends distally from hub 38 externally of housing 16 and through an end wall 36 of the housing into the proximal end 130 of the safety probe 112. Spring 44 is disposed concentrically around tube 34 and mounted in compression between flange 28 and end wall 36 such that the safety probe 112 is biased in a distal direction with operating flange 28 biased against plate 56. A valve assembly 40, such as stop cock 42, is provided on tube 34 to allow passage of fluid therethrough and for additional confirmation of cavity penetration via leakage detection and for irrigation and aspiration via apertures 132. Cannula 14 includes distal end 78 terminating at peripheral edge 82 angled at an acute angle that is the same as the angle for end surface 22 and a proximal end 84 secured to front wall 32 of housing 16.

According to a method of operation for the retractable safety penetrating instrument 110, the locking springs 66 are normally in the position shown in FIG. 8 with fingers 74 of locking bars 120 biased into engagement with plate 56 such that the retracting mechanism 48 and, therefore, the needle 12, cannot move proximally. Spring 44 is normally in the position shown in FIG. 8 such that the safety probe 112 is biased distally with flange 28 biased against plate 56 such that the distal end surface 128 of the safety probe 112 protrudes beyond and protects the sharp tip 20 of the needle 12. The distal end surface 22 of needle 12 is substantially aligned with the peripheral edge 82 of the cannula 14 presenting a substantially smooth profile for tissue penetration. Triggers 76 are in the rest position disposed in the path of movement of flange 28. When penetrating tissue T forming a wall of an anatomical cavity, the safety penetrating instrument 110 is forced into the tissue causing the safety probe 112 to move proximally against the distal bias of spring 44 due to the proximal force from tissue contact at the distal end of the retractable safety penetrating instrument such that the angled end surface 128 of the safety probe 112 will be substantially aligned with the end surface 22 of the needle 12 presenting a substantially solid configuration for penetration through the tissue. With end surface 128 aligned with end surface 22, flange 28 will have moved proximally past the triggers 76; however, the fingers 74 will remain engaged with plate 56. Upon penetration of the distal end 78 of the cannula 14 into the anatomical cavity, the safety probe 112 will move distally due to the distal bias of spring 44. As the safety probe 112 moves distally, flange 28 engages triggers 76 and pulls the triggers distally forcing arms 72 of locking springs 66 in a direction outwardly from the longitudinal axis such that the fingers 74 are pulled via the webs 124 out of engagement with plate 56 prior to end surface 128 of the safety probe 112 protruding beyond the tip 20 of the needle 12. With fingers 74 disengaged from plate 56, the needle 12 is free to move proximally due to the proximal bias of strong retracting spring 62 overriding the distal bias of spring 44, and the safety probe 112 will be moved proximally along with the needle 12 due to abutment of plate 56 with flange 28. With the needle 12 and the safety probe 112 proximally biased, the locking bars 120 will be disposed along skirt 118, and the sharp tip 20 of the needle 12 will be protected within the cannula 14. The retractable safety penetrating instrument can be reset for further use by moving knob 46 distally until plate 56 is engaged by fingers 74.

Another modification of a retractable safety penetrating instrument according to the present invention is shown in FIG. 9 at 140. The retractable safety penetrating instrument 140 includes needle 12, cannula 14 concentrically disposed around needle 12, housing 16 mounting needle 12 and coupling 142 mounting cannula 14. The coupling 142 can be latched to housing 16 with the use of any suitable releasable mechanism, allowing the housing to be removed from the coupling withdrawing the needle from the cannula. Accordingly, the retractable safety penetrating instrument 140 can be considered to be formed of a cannula unit and a penetrating member unit, the cannula unit including cannula 14 and coupling 142 and the penetrating member unit including needle 12 and housing 16. The needle 12 is cannulated and has an open distal end 18 terminating at sharp tip 20 and a cylindrical body 26 extending proximally from trailing edge 24 to an operating flange 28 at a proximal end 30 of the needle disposed in housing 16. A retracting mechanism 48 is mounted on proximal end 30 of the needle 12 and includes a rail 50 having an open distal end and a proximal end closed by an abutment wall 54 and a plate 56 extending radially from the periphery of the rail perpendicularly with a longitudinal axis of the rail. A ledge or extension 144 extends perpendicularly from plate 56 in a proximal direction and terminates at an elbow 146. A strong retracting spring 62 is mounted within rail 50, the retracting spring being mounting in compression between front wall 32 of housing 16 and abutment wall 54 to bias the retracting mechanism 48 and, therefore, the needle 12, in a proximal direction. Tube 34 extends from an end wall 36 of housing 16 in a distal direction and into the proximal end 30 of the needle 12. A valve assembly 40, such as rotatable valve 42, can be provided in end wall 32 in alignment with the lumen of tube 34 to control flow through the retractable safety penetrating instrument. A helical coil spring 44 is mounted concentrically around tube 34 and mounted in compression between operating flange 28 and end wall 36 to bias the needle 12 in a distal direction, with operating flange 28 biased against abutment wall 54. A longitudinal slot 148 is formed in the cylindrical body 26 of the needle 12 and a pin or protrusion 58 on tube 34 projects into the slot 148 to serve as a positive stop limiting proximal movement of the needle. Locking and releasing mechanism 64 is disposed in housing 16 and prevents proximal movement of the retracting mechanism 48 and, therefore, the needle 12. The locking and releasing mechanism 64 includes a latch or locking spring 66 having a substantially flat base 68 secured to a wall of housing 16, a proximal bend 70 disposed adjacent end wall 36 of the housing and an arm 72 extending angularly, distally from bend 70 in the direction of a longitudinal axis of the retractable safety penetrating instrument. Arm 72 terminates distally at a bent locking finger 74 spring biased into engagement with elbow 146 to prevent proximal movement of the retracting mechanism 48. Arm 72 has a curved section 150 disposed between finger 74 and proximal bend 70, the curve section 150 defining a clearance mounting an off-center pivot or cam 152. A release member or trigger 76 extends from a proximal portion of cam 152 toward the longitudinal axis and is biased to a rest position disposed in the path of movement of operating flange 28. Cannula 14 includes distal end 78 and proximal end 84 secured to a front wall 154 of coupling 142. The coupling 142 is preferably made of plastic to reduce cost and has a configuration in cross-section corresponding to the cross-sectional configuration of housing 16 to facilitate grasping during use. An opening is formed in an end wall 156 of the coupling allowing passage of the needle 12 through the cannula 14.

In order to assemble the retractable safety penetrating instrument 140, the proximal end 30 of the needle 12 is assembled in housing 16 as shown in FIG. 9 with the retracting mechanism 48 held against proximal movement by finger 74 engaging elbow 146. Needle 12 is biased distally by spring 44 such that operating flange 28 is biased against abutment wall 54 and is disposed distally of trigger 76. The penetrating member unit is then combined with the cannula unit by passing the needle through the coupling 142 via the opening in the end wall 156 and through the cannula 14. With the front wall 32 of housing 16 abutting the end wall 156 of the fitting the angled peripheral edge 82 of the cannula will be disposed proximally of the trailing edge 24 of the needle 12.

According to a method of operation for the retractable safety penetrating instrument 140, the locking spring 66 is normally in a position shown in FIG. 9 with finger 74 biased into engagement with elbow 146 such that the retracting mechanism 48 and, therefore, the needle 12, cannot move proximally. Spring 44 is normally in the position shown in FIG. 9 such that the needle 12 is biased distally with flange 28 biased against abutment wall 54 such that the trailing edge of the needle 12 protrudes beyond the peripheral edge 82 of the cannula 14. Trigger 76 is the rest position disposed in the path of movement of flange 28. When penetrating tissue forming a wall of an anatomical cavity, the housing and coupling are grasped in one hand and the safety penetrating instrument 140 is forced into the tissue causing the needle 12 to move proximally against the distal bias of spring 44 due to the proximal force from tissue contact at the distal end of the retractable safety penetrating instrument. The trailing edge 24 of the needle 12 will be substantially aligned with the peripheral edge 82 of the cannula 14 presenting a substantially smooth profile facilitating penetration through the tissue. Flange 28 will have moved proximally passed the trigger 76; however, the finger 74 will remain engaged with elbow 146, the pin 58 serving as a positive stop limiting proximal movement of the needle. Upon penetration of the distal end 78 of the cannula 14 into the anatomical cavity, the needle 12 will move distally due to the distal bias of spring 44 such that flange 28 engages trigger 76 and pulls the trigger distally. As trigger 76 is pulled distally, cam 152 is forced downwardly, rotating counterclockwise looking at FIG. 9, such that arm 72 is moved in a direction outwardly from the longitudinal axis. With rotation of cam 152 counterclockwise, finger 74 will be moved out of engagement with elbow 146 releasing retracting mechanism 48 such that the needle 12 is moved proximally due to the proximal bias of retracting 62 overcoming the distal bias of spring 44. With the needle 12 proximally biased, the sharp tip 20 of the needle will be protected within the cannula 14 and the operating flange 28 is positioned proximally of trigger 76. The retractable safety penetrating instrument can be reset for further use by moving knob 46 distally along the slot in housing 16 as previously described.

As shown in FIG. 10, the penetrating member unit can be withdrawn from the cannula unit leaving the cannula 14 in place in a tubular vessel or cavity C, such as a vein or artery, with the coupling 142 disposed externally of the cavity. Various other devices, such as a flexible catheter or an intravenous tube 158, can be coupled with coupling 142 via the opening in the end wall 156 for various medical procedures.

A housing for a modification of the retractable safety penetrating instrument according to the present invention is shown in FIG. 11 at 160. Housing 16 mounts a retracting mechanism 48 including a plate 56 disposed at a proximal end 30 of a needle 12 and having an aperture therein receiving tube 34 in the proximal end 30 of the needle 12. Tube 34 extends from a hub or end cap 162 to an annular rim 164 disposed within the proximal end 30 of the needle 12. A retracting spring 62 is disposed within the proximal end 30 of the needle 12 concentrically around tube 34 and mounted in compression between rim 142 and plate 56 to bias the needle in a proximal direction. A locking and releasing mechanism 64 is disposed in housing 16 to prevent proximal movement of the retracting mechanism and, therefore, the needle 12, and includes a latch or locking spring 66 mounted in the lumen of tube 34 and having a substantially flat base 68 secured to a wall of the tube 34, a proximal bend 70 extending through a longitudinal aperture 166 in the tube 34 in a distal direction angularly, outwardly from a longitudinal axis of the retractable safety penetrating instrument 160 and an arm 72 extending distally from bend 70 parallel with the longitudinal axis externally of tube 34. A finger 74 on a distal end of arm 72 is spring-biased into engagement with plate 56 and prevents proximal movement of the needle 12, and a bump or curve 168 on arm 72 projects in a direction outwardly from the longitudinal axis. A proximal end 84 of cannula 14 is mounted in housing 16, the proximal end terminating at a flange 170 disposed in housing 16. Tube 34 extends through an opening in rear wall 36 of the housing 16 such that the needle 12 extends through the cannula 14 with plate 56 disposed in the housing proximally of an intermediate wall 172. A spring 44 is disposed concentrically around the proximal end 30 of the needle 12 and is mounted in compression between flange 170 and intermediate wall 172 to bias the cannula 14 in a distal direction. A releasing or trigger member is mounted in housing 16 and includes a cam or off-center pivot 152 rotatably mounted in housing 16 on a pin 176 extending transverse to a longitudinal axis of the retractable safety penetrating instrument and having ends secured to walls of housing 16, the pin passing through the cam off-center with a longitudinal axis of the cam. As shown in FIG. 12, a spring 178 is disposed around pin 176 and is secured, respectively, to housing 16 and cam 152, the spring being wound in torsion to torsionally bias the cam to a rest position shown in FIG. 11. The cam is positioned laterally adjacent the bump 168, and a trigger 76 extends from a proximal portion of the cam in a direction outwardly from the longitudinal axis of the retractable safety penetrating instrument. An operating member including an operating or cocking arm 180 extends proximally from flange 170 through an opening in intermediate wall 172 and terminates in a hook 182 disposed distally of trigger 76. The locking spring 66 is normally in the position shown in FIG. 11 with cam 152 and trigger 76 in a rest position and finger 74 of the locking spring 66 engaging plate 56 such that the needle 12 cannot move proximally and is, therefore, locked. Spring 44 is normally in the position shown in FIG. 11 such that the cannula 14 is biased distally. During penetration of tissue, the cannula 14 will move proximally against the distal bias of spring 44 due to the proximal force from tissue contact at the distal end of the retractable safety penetrating instrument, and the cannula 14 will follow the needle 12 through the tissue. Cannula 14 will move proximally until spring 44 is compressed between flange 170 and intermediate wall 172, serving as a positive stop limiting proximal movement of the cannula, and the hook 182 on the operating arm 180 will move proximally past the trigger 76. As the hook 182 moves proximally past the trigger 76, finger 74 remains engaged with plate 56 preventing proximal movement of the needle 12. Once the distal end of the retractable safety penetrating instrument has entered the anatomical cavity, the cannula 14 will be moved distally due to the distal bias of spring 44. As the cannula 14 moves distally, hook 182 of operating arm 180 engages trigger 76 and pulls the trigger distally causing the cam to rotate clockwise looking at FIG. 11. Accordingly, the cam is forced against bump 168 moving arm 72 into aperture 166 and causing the finger 74 to be released from plate 56. Once released, the locking spring 66 will enter the aperture 166 in tube 34 and the needle 12 will be moved proximally due to the proximal bias of retracting spring 62 such that the sharp tip 20 of the needle 12 is disposed within the distal end 78 of the cannula 14. With the needle 12 biased proximally, the hook 182 on the operating arm 180 is disposed distally of the trigger 76 and the retractable safety penetrating instrument can be reset for further use as previously described.

A modification of a locking and releasing mechanism for the retractable safety penetrating instrument according to the present invention is illustrated in FIG. 13 at 190 and includes a latch or locking spring 66 having a substantially flat base 68 to be secured to a side wall of the housing and terminating proximally in a bend 70 and an arm 72 joined to bend 70 to extend angularly, distally therefrom such that a bent locking finger 74 on a distal end of the arm 72 can engage the retracting mechanism to prevent movement of the retracting mechanism in the proximal direction within housing 16. Latch 66 has a curved section 192 between bend 70 and finger 74, the curved section curving toward the base 68 to define a clearance, and a releasing or trigger member such as an off-center pivot or cam 152 is mounted in the clearance. Cam 152 is rotatable on a pin 176 extending transverse to arm 72 and having ends securable to side walls of the housing 16, the pin passing through the cam off-center with a central longitudinal axis of the cam. A trigger or leaf 76 curved in a distal direction extends from a proximal portion of the cam 152, the cam being positioned by the arm 72 such that the trigger 76 is disposed in a rest position within housing 16 proximally of the operating member 28 in the path of movement of the operating member. Although arm 72 biases the cam to the rest position, a spring (not shown) can be disposed around the pin 176 and secured to a side wall of housing 16 and the cam 152, respectively, with a torsional bias to bias the cam to the rest position. The latch 66 can be mounted at any suitable location on the housing 16 such that finger 74 acts as a stop or abutment to prevent proximal movement of the retracting mechanism 48 and to be actuated or released by the trigger 76. In operation, the operating member 28 will move proximally past the trigger 76 during penetration of tissue of a cavity wall; however, this movement will not disengage the latch 66 from the retracting mechanism 48 and the trigger 76 will return to the rest position as soon as the operating member has moved proximally there past. Upon penetration into an anatomical cavity, the operating member will move distally to engage the trigger 76 and pull the trigger distally such that the cam 152 is rotated counterclockwise looking at FIG. 13. With counterclockwise rotation, the cam 152 is forced against the latch 66 moving arm 72 outwardly in the direction of base 68 and releasing finger 74 from engagement with the retracting mechanism.

A modification of the distal end of the retractable safety penetrating instrument according to the present invention is shown in FIG. 14 at 200 and includes a needle 12 having a cylindrical body 26 terminating distally at an internally threaded socket 202 and a cannula 14 terminating distally at a peripheral edge 82 disposed proximally of the socket 202. A distal tip 204 is mounted on cylindrical body 26 and includes three, equally spaced end surfaces or facets 206 defining a pyramidal configuration and tapering distally to a sharp tip 20 and joined proximally to a cylindrical neck 208. An externally threaded shaft 210 extends proximally from neck 208 to be threadedly received in socket 202 allowing various tip configurations to be mounted on cylindrical body 26 for various medical procedures. Needle 12 can be mounted such that during penetration of tissue of a cavity wall, the needle will retract in a proximal direction such that scalloped edges or junction 212 joining facets 206 to neck 208 will be aligned with peripheral edge 82 of cannula 14. Apertures 132 are formed in facets 206 providing fluid communication with the cavity through needle 12.

FIGS. 15, 16 and 17 show modifications of distal tips 204 for mounting on cylindrical body 26. Distal tip 214 shown in FIG. 15 includes a plurality of end surfaces or facets 206 terminating proximally at scalloped edges or junction 212 joining the facets to cylindrical neck 208 with apertures 132 being formed in the facets. Externally threaded shaft 210 extends proximally from neck 208 allowing tip 214 to be secured on cylindrical body 26. A distal tip 216 shown in FIG. 16 has a conical configuration with a thread 220 disposed along the tip 216 from sharp point 20 to junction 212 joining the tip to cylindrical neck 208. Externally threaded shaft 210 extends from neck 208 for mounting on cylindrical body 26, and apertures 132 are provided on the distal tip 216 for fluid communication with an anatomical cavity. The distal tip 216 is particularly advantageous in penetrating tissue with a relatively slow, rotational motion allowing penetration into very small or narrow anatomical cavity to be accomplished with greater control and precision. The distal tip 218 shown in FIG. 17 has a conical configuration tapering to sharp tip 20 and proximally joined at junction 210 to neck 208 with aperture 132 in the distal tip 218 providing fluid communication with the anatomical cavity.

A housing for a modification of the retractable safety penetrating instrument according to the present invention is shown in FIG. 18 at 220. Housing 16 mounts a retracting mechanism 48, an operating member 28 and a locking and releasing mechanism 64 similar to that described for the retractable safety penetrating instrument 140 of FIG. 9. Tube 34 extends distally from a hub 38 disposed externally of the housing 220 and through an opening in an end wall 36 of the housing, the tube 34 extending through an opening in the operating flange 28. An opening 39 in the hub 38 communicates with the lumen of tube 34, and a valve assembly 40, such as stop cock 42, is mounted on tube 34 to control flow through the lumen of tube 34. One or more, flexible, bendable or rigid conduits or branches 222 are joined to tube 34 externally of housing 220 and terminate at open hubs 224 providing fluid communication with the lumen of tube 34 via the conduits 222. The housing arrangement 220 is particularly desirable when the cannula is a suprapubic catheter or an angio-catheter in that, upon introduction of the distal end of the cannula into an anatomical cavity, hubs 38 and 224 provide multiple branches of communication with tube 34 and, therefore, the needle, allowing aspiration, irrigation and insertion of additional instruments to be accomplished through the needle via the tube 34 and branches 222. Flow introduced via hub 38 can be controlled with the valve assembly 40; however, the housing arrangement can be used with or without a valve assembly.

As described above, it will be appreciated that the sharp tip of the penetrating member is immediately retracted within a cannula which acts as a shield upon entering a body cavity. In this manner, the safety penetrating instrument can be used to create a passage through the needle within the cannula or the cannula with the needle withdrawn and in a wide variety of procedures requiring either short cannulas, for example with a syringe or intravenous catheter, or long cannulas, for example with suprapubic or angio catheters. Additionally, injections can be safely performed with the present invention by providing a cannula over the injection needle of a syringe and utilizing a retraction mechanism to retract the needle into the cannula after penetration into a vein or other cavity. The passage produced by the cannula can accommodate fluid flow and/or the passage of long flexible instruments such as those used in angioplasty.

Many complications from introduction of a cannula into an anatomical cavity with a needle result from the surgeon not using a smooth, continuous movement in forcing the needle through the cavity wall. That is, when the needle movement is jerky or not smoothly continuous, entry into the cavity is frequently accomplished with too much force resulting in undesirable contact with tissue or organ structures in the cavity even if safety penetrating instruments are used; and, additionally, a jerky, discontinuous movement creates uneven tissue tearing rather than the minimal incision sought. One of the advantages of the present invention is that use of the retractable safety penetrating instrument encourages a smooth, continuous penetrating movement by the surgeon in that, should the surgeon use a jerky penetrating movement, the needle will retract within the cannula due to the proximal movement of the retractable safety penetrating instrument by the surgeon. That is, when the surgeon moves the retractable safety penetrating instrument proximally or rearwardly, as occurs when the surgeon is hesitant or unsure, the operating member will move distally to trigger retraction of the needle. Thus, the retractable safety penetrating instrument not only provides safe penetration of an anatomical cavity but also assures proper use of the penetrating instrument to minimize trauma.

The retractable safety penetrating instrument of the present invention includes a cannula receiving a needle having a sharp distal tip protruding beyond a distal end of the cannula for penetrating tissue and retractable to a protected position via a trigger responsive to movement of the retractable safety penetrating instrument distally upon entering a body cavity. The needle or cannula can be biased distally by springs or other suitable devices for applying a biasing force, and biasing devices can be mounted within, around or laterally of the needle and the cannula. The retracting spring for moving the needle proximally can be mounted externally of, concentrically around or within the needle, and various rail configurations can be employed to mount the retracting spring externally of the needle. A variety of positive stop configurations can be utilized to limit proximal movement of the needle or cannula during penetration of tissue, and the positive stop can be provided at the distal end or the proximal end of the retractable safety penetrating instrument. A locking mechanism for preventing movement of the needle proximally can include a variety of latches or springs, and the release mechanism can include cams, spring-like members or any suitable means for releasing the locking mechanism by an action to move the latch or lock member out of the path of movement of the needle or a rail movable therewith, such as in camming, spring, bending or buckling type actions and the like. The locking and releasing mechanism can be of multi-part or integral, unitary construction and can be disposed within a unitary or multi-part housing. The needle must be securely held or locked in position prior to triggering of the retraction mechanism; and, thus, the latch members are preferably secured to the housing and can include multi-part or unitary flexible spring members operated by leaves or cams as well as pivoted rigid members secured to the housing. The operating member for engaging the trigger can be provided on the needle, the cannula or an inner probe disposed within the needle. Where the operating member includes a probe disposed within the needle, the probe can extend beyond the sharp tip of the needle to protect the sharp tip prior to penetration of a cavity wall. In this manner, the inner probe protects the sharp tip prior to use while also causing retraction of the needle after penetration into the cavity. The sharp distal end of the needle can have various solid or hollow geometrical configurations, and the distal end of the needle can be interchangeably mounted on the cylindrical body thereof.

Having described preferred and alternative embodiments of a new and improved retractable safety penetrating instrument, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A retractable safety penetrating instrument for introduction into a cavity in the body comprising
 a cannula having a distal end for positioning in the body cavity, a proximal end for positioning externally of the body cavity and a lumen extending between said distal and proximal ends;
 a tubular needle slidably disposed in said cannula lumen and having a sharp distal tip for penetrating a wall of the cavity;
 retracting means for moving said sharp distal tip proximally from an extended position where said sharp distal tip protrudes beyond said cannula distal end to a retracted position where said sharp distal tip is withdrawn into said cannula to prevent contact of said sharp distal tip with tissue; and
 trigger means including an operating member movable distally when said sharp distal tip has penetrated into said cavity and a trigger member for being engaged by said operating member when said operating member moves distally for automatically actuating said retracting means to move said sharp distal tip to said retracted position.

2. A retractable safety penetrating instrument as recited in claim 1 and further comprising means for permitting said needle to move proximally as said needle penetrates the cavity wall and wherein said operating member is disposed on said needle.

3. A retractable safety penetrating instrument as recited in claim 1 and further comprising an inner member disposed within said needle and means for permitting said inner member to move proximally as said needle penetrates the cavity wall and wherein said operating member is disposed on said inner member.

4. A retractable safety penetrating instrument as recited in claim 3 wherein said inner member includes an angled distal end surface and said needle includes an angled distal end surface at said sharp distal tip and wherein said inner member distal end surface is aligned with said needle distal end surface as said needle penetrates the cavity wall.

5. A retractable safety penetrating instrument as recited in claim 1 and further comprising means for permitting said cannula to move proximally as the needle penetrates the cavity wall and wherein said operating member is disposed on said cannula.

6. A retractable safety penetrating instrument as recited in claim 1 wherein said retracting means includes means for biasing said needle proximally and further including locking means engageable with said retracting means for preventing movement of said sharp distal tip proximally, said trigger means further including releasing means for being engaged by said operating member when said operating member moves distally for disengaging said locking means from said retracting means.

7. A retractable safety penetrating instrument for introduction into a cavity in the body comprising a cannula having a distal end for positioning in the body cavity, a proximal end for positioning externally of the body cavity and a lumen extending between said distal and proximal ends;

a tubular needle slidably disposed in said cannula lumen and having a sharp distal tip for penetrating a wall of the cavity;

retracting means for moving said needle proximally from an extended position where said sharp distal tip protrudes beyond said cannula distal end to a retracted position where said sharp distal tip is withdrawn into said cannula to prevent contact of said sharp distal tip with tissue, said retracting means including means for biasing said needle proximally;

locking means engageable with said retracting means for preventing movement of said retracting means proximally, said locking means including a latch biased into engagement with said retracting means; and trigger means including an operating member movable distally when said sharp tip has penetrated into said cavity for automatically actuating said retracting means to move said needle to said retracted position, said trigger means including releasing means for being engaged by said operating member when said operating member moves distally for disengaging said locking means from said retracting means.

8. A retractable safety penetrating instrument as recited in claim 7 wherein said latch includes a spring.

9. A retractable safety penetrating instrument as recited in claim 8 wherein said releasing means includes cam means for disengaging said latch from said retracting means.

10. A retractable safety penetrating instrument as recited in claim 9 wherein said releasing means further includes a trigger on said cam means for being engaged by said operating member when said operating member moves distally.

11. A retractable safety penetrating instrument as recited in claim 10 wherein said cam means is biased to a rest position wherein said trigger is disposed within the path of distal movement of said operating member.

12. A retractable safety penetrating instrument as recited in claim 8 wherein said releasing means includes spring means and a trigger on said spring means biased into the path of distal movement of said operating member.

13. A retractable safety penetrating instrument as recited in claim 7 wherein said latch includes a locking bar and said releasing means includes spring means for biasing said locking bar into engagement with said retracting means and disengaging said locking bar from said retracting means, said releasing means further including a trigger biased into the path of distal movement of said operating member.

14. A retractable safety penetrating instrument as recited in claim 7 wherein said locking means and said releasing means are of integral, unitary construction.

15. A retractable safety penetrating instrument as recited in claim 7 wherein said locking means and said releasing means are of multi-part construction.

16. A retractable safety penetrating instrument for introduction into a tubular vessel in the body comprising a cannula having a distal end for positioning in the tubular vessel, a proximal end for positioning externally of the tubular vessel and a lumen extending between said distal and proximal ends;

a tubular needle disposed in said lumen of said cannula and having a sharp distal end for penetrating the wall of the tubular vessel;

retracting means for moving said sharp distal end proximally relative to the cannula from an extended position where said sharp distal end protrudes beyond said cannula distal end to a retracted position where said sharp distal end is disposed within said cannula distal end; and trigger means for automatically actuating said retracting means to move said sharp distal end to said retracted position in response to movement of said needle distally upon said cannula distal end entering the tubular vessel whereby said sharp distal end of said needle is protected from inadvertent contact with tissue in the tubular vessel.

17. A retractable safety penetrating instrument as recited in claim 16 wherein said retracting means includes means for biasing said needle in a proximal direction.

18. A retractable safety penetrating instrument as recited in claim 17 further including means engageable with said retracting means for preventing movement of said needle in the proximal direction and said trigger means includes means for automatically disengaging said movement preventing means.

19. A retractable safety penetrating instrument for introduction into a tubular vessel in the body comprising a cannula having a distal end for positioning in the tubular vessel, a proximal end for positioning externally of the tubular vessel and a lumen extending between said distal and proximal ends;

a tubular needle disposed in said lumen of said cannula and having a sharp distal end for penetrating the wall of the tubular vessel and a hollow proximal end;

retracting means for moving the needle proximally relative to the cannula from an extended position where said sharp distal end protrudes beyond said cannula distal end to a retracted position where said sharp distal end is disposed within said cannula distal end, said retracting means including means for biasing said needle in a proximal direction;

means engageable with said retracting means for preventing movement of said needle in the proximal direction;

trigger means for automatically actuating said retracting means to move said needle to said retracted position in response to movement of said retractable safety penetrating instrument distally upon said cannula distal end entering the tubular vessel whereby said sharp distal end of said needle is protected from inadvertent contact with tissue in the tubular vessel, said trigger means including means for automatically disengaging said movement preventing means; and housing means for mounting said proximal end of said needle and cylindrical member means secured to said housing means and extending into said needle proximal end for guiding proximal movement of said needle.

20. A retractable safety penetrating instrument as recited in claim 19 wherein said biasing means includes a spring disposed within said needle concentrically around said cylindrical member means.

21. A retractable safety penetrating instrument as recited in claim 20 further including a rim on said cylindrical member means disposed within said proximal end of said needle and a plate on said proximal end of said needle, said spring being mounted in compression between said rim and said plate.

22. A retractable safety penetrating instrument as recited in claim 19 wherein said biasing means is disposed within said housing means externally of said needle.

23. A retractable safety penetrating instrument as recited in claim 22 further including rail means mounted externally on said proximal end of said needle and having an abutment wall, and said biasing means includes a spring mounted in compression between said housing means and said abutment wall.

24. A retractable safety penetrating instrument as recited in claim 23 further including plate means extending from said rail means and having an aperture therein for receiving said proximal end of said needle.

25. A retractable safety penetrating instrument as recited in claim 24 further including pin means on said rail means for providing a positive stop limiting proximal movement of said needle.

26. A retractable safety penetrating instrument as recited in claim 24 further including a tube secured to said housing means and extending into said proximal end of said needle, longitudinal slot means in said proximal end of said needle and pin means on said tube received within said slot means for providing a positive stop limiting proximal movement of said needle.

27. A retractable safety penetrating instrument as recited in claim 19 wherein said biasing means includes a spring disposed concentrically around said needle.

28. A retractable safety penetrating instrument as recited in claim 27 further including a plate mounted on said proximal end of said needle and an annular skirt disposed concentrically around said needle and extending from said plate, said spring being disposed concentrically around said needle within said skirt and maintained in compression between said housing means and said plate.

29. A retractable safety penetrating instrument for providing fluid communication with a cavity in the body comprising
a cannula for providing a passage through a cavity wall and having a distal end for positioning in the body cavity, a proximal end for positioning externally of the body cavity and a lumen extending between said distal and proximal ends;
a tubular needle having a sharp distal end for penetrating the cavity wall; and
means for mounting the needle in said lumen of said cannula for allowing proximal movement of said needle relative to said cannula during penetration of the cavity wall, said means for mounting including means for biasing said needle in a distal direction to allow proximal movement of said needle against the distal bias in response to a proximal force from tissue contact at said distal end of said needle during penetration of the cavity wall.

30. A retractable safety penetrating instrument as recited in claim 29 wherein said needle includes a proximal end and further including a housing mounting said needle proximal end and a flange on said needle proximal end disposed in said housing and wherein said distal biasing means includes a spring mounted in compression between said flange and said housing.

31. A retractable safety penetrating instrument as recited in claim 30 wherein said housing includes an end wall and said needle proximal end is hollow and further including a tube extending from said end wall into said proximal end of said needle, said spring being disposed concentrically around said tube.

32. A retractable safety penetrating instrument as recited in claim 31 wherein said needle distal end includes an end surface tapering to a sharp tip and a cylindrical body joined to said end surface at a trailing edge and said cannula distal end includes a peripheral edge, said trailing edge being aligned with said peripheral edge when said needle moves proximally against the distal bias in response to a proximal force from tissue contact at said distal end of said needle to present a substantially smooth profile.

33. A retractable safety penetrating instrument as recited in claim 32 further including positive stop means for limiting proximal movement of said needle against said distal bias.

34. A retractable safety penetrating instrument as recited in claim 33 wherein said positive stop means is disposed at said proximal end of said needle.

35. A retractable safety penetrating instrument for introduction into a cavity in the body comprising
a cannula having a distal end for positioning in the body cavity, a proximal end for positioning externally of the body cavity and a lumen extending between said distal and proximal ends;
a tubular needle disposed in said lumen of said cannula having a sharp distal end for penetrating the cavity wall;
means for biasing said needle distally within said lumen of said cannula to an extended position where said sharp distal end protrudes beyond said cannula distal end;
retracting means for moving said needle proximally relative to said cannula from said extended position to a retracted position to prevent contact of said sharp distal end with tissue; and
trigger means for automatically actuating said retracting means to move said needle to said retracted position in response to movement of said needle distally within said lumen of said cannula.

36. A retractable safety penetrating instrument as recited in claim 35 further including means for selectively moving said needle from said retracted position to said extended position.

37. A retractable safety penetrating instrument as recited in claim 36 wherein said means for selectively moving includes knob means on said needle, housing means for mounting said needle and slot means in said housing means for receiving said knob means, said knob means being movable along said slot means to move said needle from said retracted position to said extended position.

38. A retractable safety penetrating instrument as recited in claim 37 further including means for selectively locking said needle in said extended position.

39. A retractable safety penetrating instrument as recited in claim 38 wherein said means for locking includes a locking member pivotably mounted on said housing means for being selectively moved into a position preventing proximal movement of said knob means along said slot means.

40. A retractable safety penetrating instrument as recited in claim 35 further including a tube extending through said housing means and into said proximal end of said needle and a hub mounting said tube externally of said housing means.

41. A retractable safety penetrating instrument as recited in claim 40 further including a valve mounted externally of said housing for controlling flow through said tube.

42. A retractable safety penetrating instrument as recited in claim 40 further including at least one conduit mounted externally of said housing in fluid communication with said tube.

* * * * *